United States Patent
Harding et al.

(10) Patent No.: US 8,625,740 B2
(45) Date of Patent: Jan. 7, 2014

(54) SYSTEM AND METHOD FOR CORRECTING X-RAY DIFFRACTION PROFILES

(75) Inventors: Geoffrey Harding, Hamburg (DE); Gabriel Zienert, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 347 days.

(21) Appl. No.: 13/087,191

(22) Filed: Apr. 14, 2011

(65) Prior Publication Data
US 2012/0263275 A1 Oct. 18, 2012

(51) Int. Cl.
*G01N 23/20* (2006.01)

(52) U.S. Cl.
USPC .......................... 378/71; 378/207

(58) Field of Classification Search
USPC .............. 378/207, 90, 71, 82, 83
See application file for complete search history.

(56) References Cited

U.S. PATENT DOCUMENTS

| | | | |
|---|---|---|---|
| 6,845,147 B2 | 1/2005 | Elam et al. | |
| 7,065,175 B2 | 6/2006 | Green | |
| 7,092,485 B2 | 8/2006 | Kravis | |
| 7,283,613 B2 | 10/2007 | Harding | |
| 7,492,863 B2 | 2/2009 | Harding | |
| 7,516,031 B2 | 4/2009 | Kogan | |
| 7,764,764 B2 | 7/2010 | Harding | |
| 7,773,724 B2 | 8/2010 | Harding | |
| 7,901,136 B2 | 3/2011 | Harding | |
| 7,924,977 B2 | 4/2011 | Harding | |
| 2008/0226019 A1* | 9/2008 | Thran et al. | 378/7 |
| 2010/0246768 A1 | 9/2010 | Toraya et al. | |

* cited by examiner

*Primary Examiner* — Hoon Song
(74) *Attorney, Agent, or Firm* — Armstrong Teasdale LLP (57) ABSTRACT

A method for correcting an X-ray diffraction (XRD) profile measured by an X-ray diffraction imaging (XDi) system is provided. The XDi system includes an anode, a detector, and a control system. The method includes obtaining an emission spectrum of the anode using the control system. The emission spectrum includes spectral structures. The method further includes calculating a piecewise spectral-correction function using the spectral structures in the emission spectrum, obtaining a measured spectrum of an object, and applying the spectral-correction function to the measured spectrum to generate a spectrally-corrected measured spectrum.

18 Claims, 7 Drawing Sheets

SYSTEM AND METHOD FOR CORRECTING X-RAY DIFFRACTION PROFILES

BACKGROUND OF THE INVENTION

The embodiments described herein relate generally to correction methods X-ray diffraction profiles and, more particularly, to energy-based and angular-variation-based correction methods for X-ray diffraction profiles.

At least some known detection systems are used at travel checkpoints to inspect containers, such as carry-on luggage and/or checked luggage, for concealed contraband, such as weapons, narcotics, and/or explosives. At least some such detection systems include X-ray imaging systems. An X-ray imaging system includes an X-ray source that transmits X-rays through a container towards a detector. An output of the detector is processed to identify a set of objects and/or materials within the container. In addition, at least some known detection systems include X-ray diffraction imaging (XDi) systems. At least some known XDi systems use inverse fan-beam geometry (a large source and a small detector) and a multi-focus X-ray source (MFXS) to detect objects and/or materials. Further, some known XDi systems provide an improved discrimination of materials, as compared to that provided by other known X-ray imaging systems, by measuring d-spacings between lattice planes of micro-crystals in materials. X-ray diffraction (XRD) may also yield data from a molecular interference function that may be used to identify other materials, such as liquids, in the container.

Some known energy-dispersive XRD profiles that are measured with an electron impact X-ray source are normalized against an emission spectrum of the X-ray source to remove spectral structures, such as anode K characteristic lines and/or a non-uniform form of bremsstrahlung background. However, such known normalization significantly increases noise in the XRD profile, even when a primary spectrum of the X-ray source is substantially noise free. Further such known normalization suppresses genuine XRD peaks within a region where a bremsstrahlung curve has its peak intensity.

A non-uniform emission spectrum of an electron impact X-ray source, or primary spectrum, is directly reflected in a shape of its energy-dispersive XRD profile. Such non-uniformity of the emission spectrum arises in two separate ways. First, a K alpha line, a K beta line, and a K edge of an anode of the X-ray source are characteristic effects arising from an interaction of high-energy electrons from a cathode with K shell electrons orbiting nuclei of the anode. Second, the bremsstrahlung or continuous component of the emission spectrum has non-uniformity originating from an interaction of high-energy electrons from the cathode with an electric field of the anode nuclei. In order to avoid adverse effects of the non-uniform primary spectrum on measured XRD spectra, the measured XRD spectra are often normalized against the primary spectrum.

One known process of normalizing the measured XRD profile against the non-uniform primary spectrum essentially multiplies the measured XRD profile by varying weighting factors. For example, if a signal in a k-th channel of the measured spectrum is $S_k$ and a weighting factor for this channel is $w_k$, a noise-to-signal ratio (NSR) can be calculated using the following equation, where RMS denotes the root mean square deviation:

$$\frac{\text{RMS Noise}}{\text{Signal}} = \frac{\left[\left\langle \sum_k S_k w_k^2 \right\rangle\right]^{1/2}}{\left\langle \sum_k S_k w_k \right\rangle}. \quad \text{(Eq. 1)}$$

For Poisson statistics that govern photon scattering experiments, a minimum NSR is achieved when all of the weighting factors are equal to one another. As such, a compromise is made when correcting for the disturbing effects of the primary spectrum on the measured XRD profile. On one hand, removing non-uniformities from the measured XRD profile improves feature extraction and/or substance identification. On the other hand, known normalization processing effectively increases noise in the measured XRD data, especially for lower density objects, even when the primary spectrum form is substantially noise free. As such, known normalization processing may reduce detection rates and/or increase false alarms.

Further, at least some known detection systems have a multiple-inverse fan-beam (MIFB) XDi topology, which has approximately 10% variation in an angle of scatter during a scan. Such scatter angle variations affect both the abscissa (momentum) and ordinate (intensity) scales of measured spectra. Further, at least some known XRD profile databases used with MIFB XDi systems include XRD profiles of known substances acquired at a reference scatter angle $\theta_R$. When the actual scatter angle of the measured spectra vary from the reference scatter angle $\theta_R$, the scanned object may not be accurately identified.

In known MIFB XDi systems, a certain object voxel is traversed by primary rays from several different X-ray source foci I directed to corresponding detector elements J. An actual angle of scatter $\theta_{IJ}$ is given by the relationship:

$$\theta_{IJ} = \theta \cdot \cos \gamma \quad \text{(Eq. 2)}$$

where $\gamma$ is an angle that a primary ray from the I-th focus to the J-th detector element makes with an X-axis, and $\theta$ is an ideal scatter angle. In one example, $\cos \gamma$ has a minimum value of ~0.9 and, as such, the actual angle of scatter $\theta_{IJ}$ is reduced relative to its maximum value by this proportion.

The relationship between momentum transfer x and the actual scatter angle $\theta$ is:

$$x = \frac{E}{h\,c} \cdot \sin\left(\frac{\theta}{2}\right) \quad \text{(Eq. 3)}$$

where E is photon energy, h is Planck's constant, and c is the speed of light. As such, the correct value of $\theta_{IJ}$ from Equation 2 is incorporated into Equation 3 to correctly transform the photon energy scale E into a momentum scale x. However, because the primary spectrum is non-uniform, it is not sufficient to only transform the energy scale E into a correct momentum scale x. More specifically, the photon intensity at energy $E_1$ corresponding to a momentum x for an angle $\theta_1$ is different than the photon intensity at energy $E_2$ corresponding to the same momentum x for an angle $\theta_2$. However, the above-described known method does not transform a photon intensity scale to produce measured XRD profiles that are comparable to the reference XRD profiles.

BRIEF SUMMARY OF THE INVENTION

In one aspect, a method for correcting an X-ray diffraction (XRD) profile measured by an X-ray diffraction imaging (XDi) system is provided. The XDi system includes an anode, a detector, and a control system. The method includes obtaining an emission spectrum of the anode using the control system. The emission spectrum includes spectral structures. The method further includes calculating a piecewise spectral-correction function using the spectral structures in the emission spectrum, obtaining a measured spectrum of an object, and applying the spectral-correction function to the measured spectrum to generate a spectrally-corrected measured spectrum.

In another aspect, a control system for use with an X-ray diffraction imaging (XDi) system is provided. The XDi system includes a radiation source configured to generate a primary beam of radiation, wherein the radiation source has an anode, and a detector configured to detect radiation scattered by an interaction of the primary beam with an object. The control system is configured to obtain an emission spectrum of the anode, wherein the emission spectrum including spectral structures, calculate a piecewise spectral-correction function using the spectral structures in the emission spectrum, obtain a measured spectrum of an object, and apply the spectral-correction function to the measured spectrum to generate a spectrally-corrected measured spectrum.

In yet another aspect, an X-ray diffraction imaging (XDi) system is provided. The XDi system includes a radiation source configured to generate a primary beam of radiation, wherein the radiation source has an anode, a detector configured to detect radiation scattered by an interaction of the primary beam with an object, and a control system coupled in communication with the detector. The control system is configured to obtain a measured spectrum detected by the detector at a first scatter angle, perform a spectral-correction procedure on the measured spectrum to remove spectral structures from an emission spectrum of the anode, and perform an angular-correction procedure on the measured spectrum to transform the measured spectrum from the first scatter angle to a second scatter angle.

BRIEF DESCRIPTION OF THE DRAWINGS

FIGS. 1-7 show exemplary embodiments of the system and methods described herein.

DETAILED DESCRIPTION OF THE INVENTION

The embodiments described herein provide a low-noise spectral-correction procedure and an angular-variation correction procedure that can be used in conjunction with the spectral-correction procedure. The spectral-correction procedure makes use of a priori knowledge of energies of the K lines and K edge of an anode to derive a corrected X-ray diffraction XRD profile that would have been measured in the absence of K structures of the anode. In addition to being low-noise, the spectral-correction procedure significantly enhances amplitudes of measured XRD peaks near a maximum in a bremsstrahlung curve as compared with the previous correction procedures.

Of the two types of beam non-uniformity discussed above, the non-uniformity associated with K structures is the more serious of the two. As such the spectral-correction procedure described herein removes the K structure non-uniformity without removing the bremsstrahlung non-uniformity. Such an approach is taken for three main reasons. First, the K peaks and the K edge interfere more with detection of Bragg peaks in the measured spectrum than does the smoothly varying bremsstrahlung component. Second, a ratio of a number of photons under the K peaks to a total number of photons in the measured spectrum is only about 10%. As such, the K structures can be removed without appreciably degrading a signal-to-noise ratio. Third, there is a satisfactory theory, such as Kuhlenkampff's equation, describing a shape of the continuous component of non-uniformity, so an effect of the continuous component can be corrected for, if necessary.

Further, the angular-variation correction procedure described herein transforms energy-dispersive XRD spectra to a common intensity and momentum scale, irrespective of actual scatter angle. As such, the angular-variation correction procedure correctly transforms both the energy and intensity of the photon spectrum from an electron impact X-ray source. Accordingly, the herein-described angular-variation correction procedure can transform a measured XRD spectrum at any actual scatter angle $\theta$ to a reference scatter angle.

Figure 1:
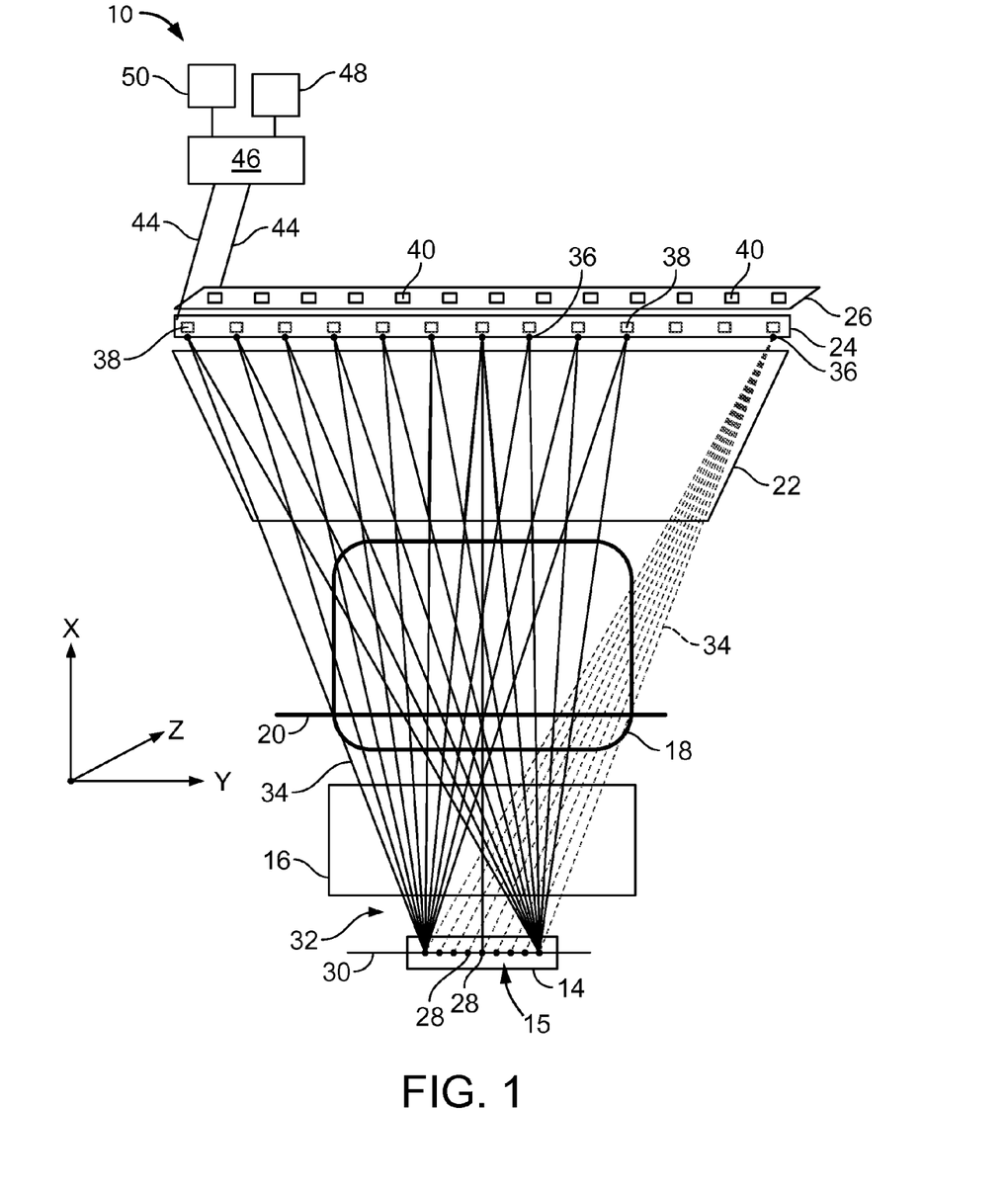
FIG. 1 is a schematic view of an exemplary embodiment of a detection system substantially in an X-Y plane.
Figure 2:
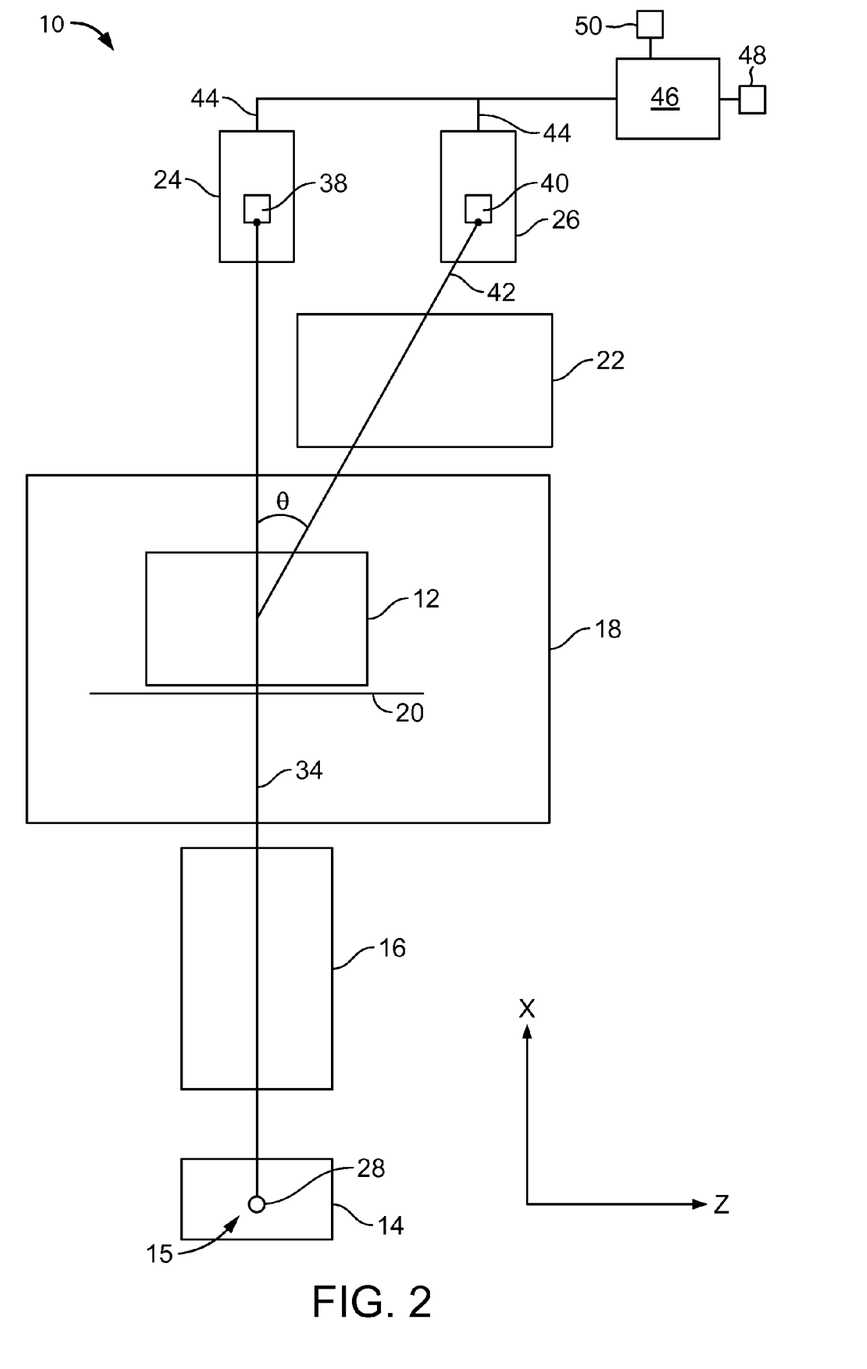
FIG. 2 is a schematic view of the detection system shown in FIG. 1 in an X-Z plane.

FIG. 1 is a schematic view of an exemplary detection system 10 in substantially an X-Y plane. FIG. 2 is a schematic view of detection system 10 in an X-Z plane. An object 12 located in detection system 10 is shown in FIG. 2, but object 12 is omitted from FIG. 1 for clarity. In the exemplary embodiment, detection system 10 is a multiple-inverse fan-beam X-ray diffraction imaging (MIFB XDi) system. Detection system 10 includes a multi-focus X-ray source (MFXS) 14 having an anode 15, a primary collimator 16, an object space 18, a support 20, a secondary collimator 22, a transmission detector 24, and a scatter detector 26. Scatter detector 26 is offset in a Z-axis direction from transmission detector 24, as shown in FIG. 2.

In the exemplary embodiment, transmission detector 24 includes a plurality of detector elements 38. More specifically, detector elements 38 are each configured to detect radiation from primary rays 34 that are transmitted through object 12 within object space 18. Furthermore, scatter detector 26 includes a plurality of scatter detector elements 40 that are configured to detect coherent scattered radiation 42 generated when a primary ray 34 interacts with object 12.

MFXS 14 is located on a lower support surface, such as a floor, while transmission detector 24 and scatter detector 26 are located on an upper support structure, such as a ceiling. In an alternative embodiment, MFXS 14 is located on the upper support structure, and transmission detector 24 and scatter detector 26 are located on the lower support surface. Furthermore, in the exemplary embodiment, MFXS 14, transmission detector 24, and scatter detector 26 are stationary, and support 20 is a conveyor belt capable of movement backward and forward in a direction substantially parallel to a Z-axis. In the exemplary embodiment, object space 18 is defined between transmission detector 24 and MFXS 14. In one embodiment, object space 18 is a baggage tunnel through which the conveyor belt moves. In an alternative embodiment, MFXS 14, transmission detector 24, and scatter detector 26 are capable of coordinated movement at least in a direction substantially parallel to the Z-axis, and support 20 is stationary. In certain alternative embodiments, MFXS 14, transmission detector 24, scatter detector 26, and support 20 are each capable of moving.

In the exemplary embodiment, MFXS 14 is configured to emit X-ray radiation sequentially or simultaneously from a plurality of focus points 28 distributed along MFXS 14 in a direction substantially parallel to a Y-axis. In the exemplary embodiment, MFXS 14 has focus points 28. In the exemplary embodiment, MFXS 14 has any suitable number of focus points 28 that enables detection system 10 to function as herein described. Detection system 10 is designed such that each focus point 28 lies at a point on a straight line 30 that is substantially parallel to the Y-axis.

Referring to FIGS. 1 and 2, MFXS 14 is, in the exemplary embodiment, configured to emit, through primary collimator 16, a set 32 of primary rays 34 of radiation from each focus point 28. In one embodiment, primary rays 34 are X-ray pencil beams generated from each focus point 28 of MFXS 14. More specifically, in the exemplary embodiment, each primary ray 34 of each set 32 is directed at a corresponding target point 36 of a plurality of target points 36 which lie in the same X-Y plane as MFXS 14. Further, each target point 36 is positioned at the same X-coordinate value, but at different Y-coordinate values. In the exemplary embodiment, each target point 36 is located at a detector element 38 of transmission detector 24. As such, each detector element 38 is configured to detect one primary ray 34 from each focus point 28.

A portion of the X-ray radiation from each primary ray 34 typically is scattered in various directions upon interaction with object 12 in object space 18. Secondary collimator 22 is configured to facilitate ensuring that a portion of scattered radiation 42 arriving at each scatter detector element 40 has a constant scatter angle θ with respect to corresponding primary ray 34 from which scattered radiation 42 originated. For example, secondary collimator 22 is configured to absorb scattered radiation that is not parallel to the direction of scattered radiation 42. Further, although in the exemplary embodiment secondary collimator 22 and scatter detector elements 40 are positioned on one side of primary rays 34 with respect to the Z-axis, in alternative embodiments secondary collimator 22 and scatter detector elements 40 may be positioned on the other side, or on both sides, of primary rays 34 with respect to the Z-axis.

In the exemplary embodiment, transmission detector 24 and scatter detector 26 are in electronic communication with a number of channels 44. In a particular embodiment, the number of channels 44 is selected based on the configuration of detection system 10. In the exemplary embodiment, channels 44 electronically communicate data collected by transmission detector 24 and each scatter detector element 40 to a control system 46. Control system 46 combines an output from transmission detector 24 and outputs from scatter detector elements 40 to generate information about object 12 within object space 18. For example, but not by way of limitation, control system 46 may generate multi-view projections, section images, and/or an X-ray diffraction (XRD) profile of object 12 to facilitate identifying a location in the container of specific materials detected by XDI analysis. Images, information, results, alarms, and/or any other suitable data generated by control system 46 can be output to a display 48 and/or a storage device 50.

For example, control system 46 stores data, an XRD profile, and/or an image in storage device 50. Examples of storage device 50 include a nonvolatile memory, such as a read only memory (ROM), and a volatile memory, such as a random access memory (RAM). Other examples of storage device 50 include a floppy disk, a compact disc-ROM (CD-ROM), a magneto-optical disk (MOD), and a digital versatile disc (DVD). Further, control system 46 also receives commands and scanning parameters from an operator (not shown) via an operator console (not shown). Display 48 allows the operator to observe an XRD profile and other data from control system 46. The operator supplied commands and parameters are used by control system 46 in operation of components of detection system 10. Moreover, in the exemplary embodiment, control system 46 uses computer algorithms to analyze a generated XRD profile with XRD profiles of known contraband materials. If a match is found, control system 46 sounds an alarm and/or displays an image of object 12 on display 48 such that the operator may view the image to determine whether a real threat exists.

Control system 46 is not limited to only those integrated circuits referred to in the art as a control system, but broadly refers to a controller, a computer, a processor, a microcontroller, a microcomputer, a programmable logic controller, an application specific integrated circuit, firmware, a circuit, software, and/or any other programmable circuit. Control system 46 may be a portion of a central control unit (not shown) or may be a stand-alone component. Further, control system 46 is configured to perform the methods described herein.

Figure 3:
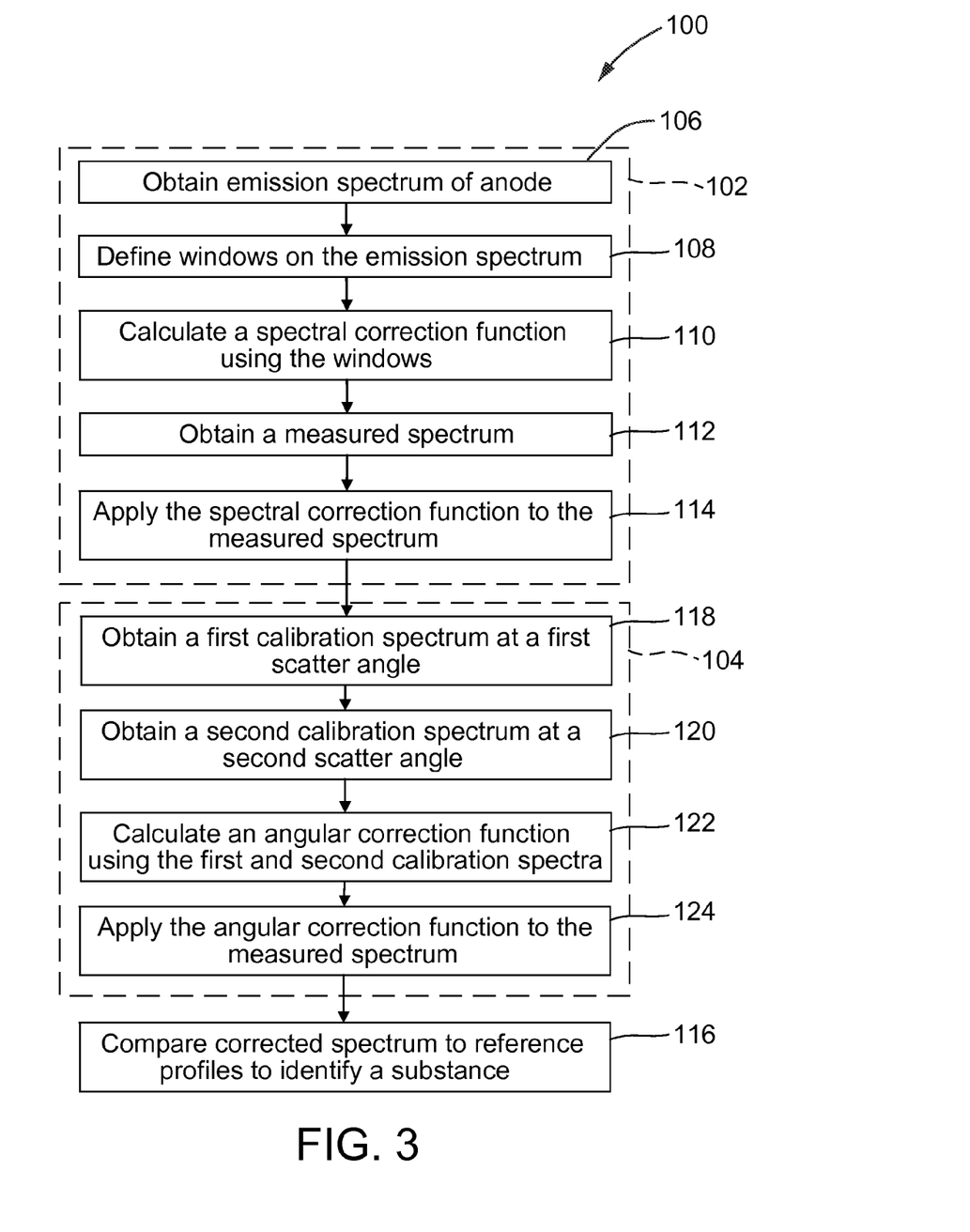
FIG. 3 is a flowchart of an exemplary correction method that may be used with the detection system shown in FIGS. 1 and 2.

FIG. 3 is a flowchart of an exemplary correction method 100 that may be performed using detection system 10 (shown in FIGS. 1 and 2). By performing method 100, projection data representing object 12 (shown in FIG. 2) can be collected and an image of object 12 can be reconstructed. Method 100 is performed at least partially by control system 46 (shown in FIGS. 1 and 2) sending or transmitting commands and/or instructions to components of detection system 10, such as storage device 48 (shown in FIGS. 1 and 2), display 50 (shown in FIGS. 1 and 2), and/or any other suitable component. A processor and/or controller within control system 46 is programmed with code segments configured to perform method 100. Alternatively, method 100 is encoded on a computer-readable medium that is readable by control system 46. In such an embodiment, control system 46 is configured to read the computer-readable medium for performing method 100.

In the exemplary embodiment, method 100 includes a noise-correction procedure 102 and an angular-variation-correction procedure 104. In one embodiment, noise-correction, or spectral-correction procedure 102 is performed without performing angular-variation-correction procedure 104. In an alternative embodiment, angular-variation-correction procedure 104 is performed without performing noise-correction procedure 102. Further, although a tungsten anode tube is described herein with respect to method 100, it should be understood that method 100 can be used with any suitable anode. When another type of anode is used with method 100, energy values and/or photon density will vary from the energy values and photon densities described herein.

Figure 4:
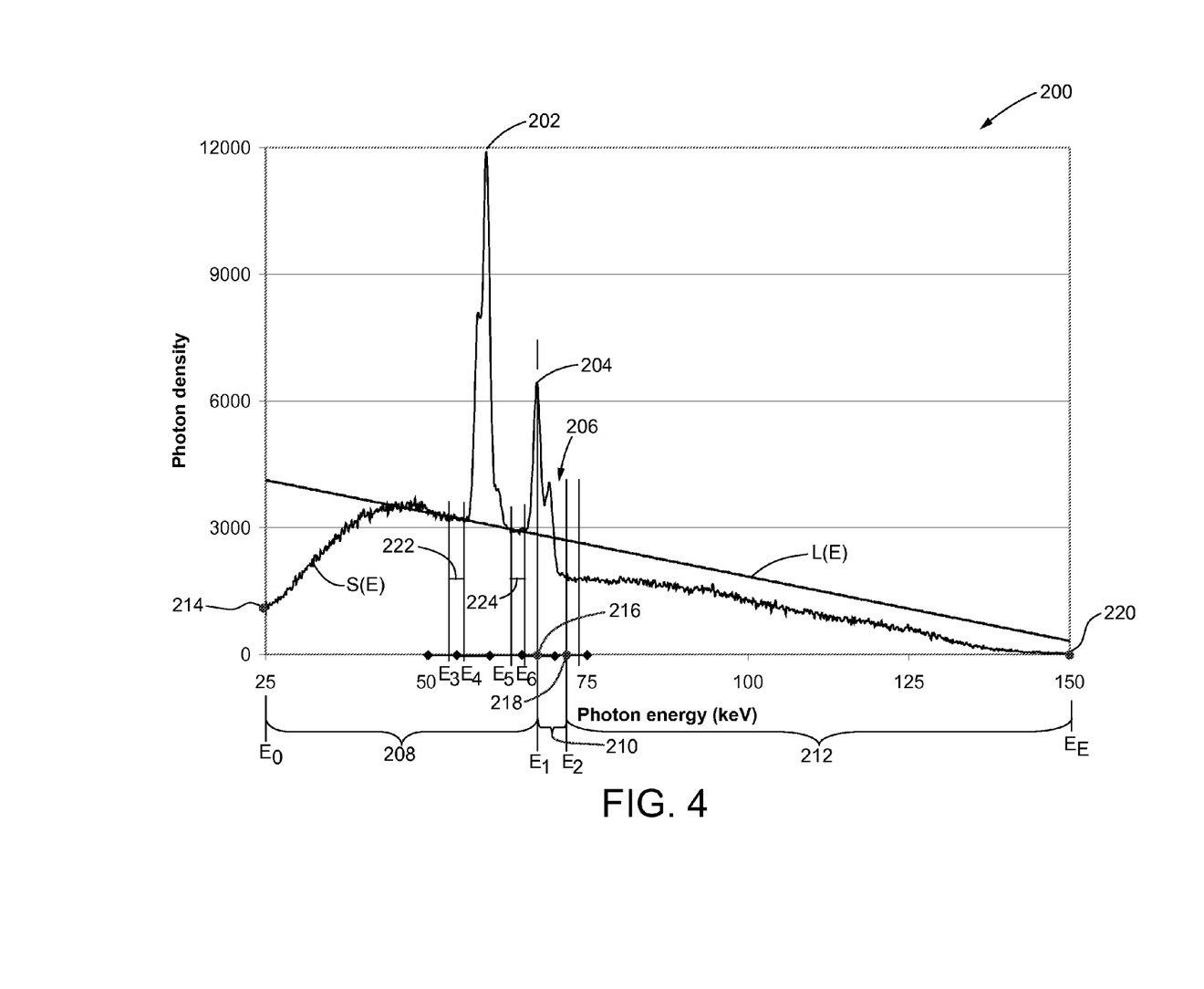
FIG. 4 is a graph of a photon density emission spectrum of a tungsten anode tube that may be used with the detection system shown in FIGS. 1 and 2.
Figure 5:
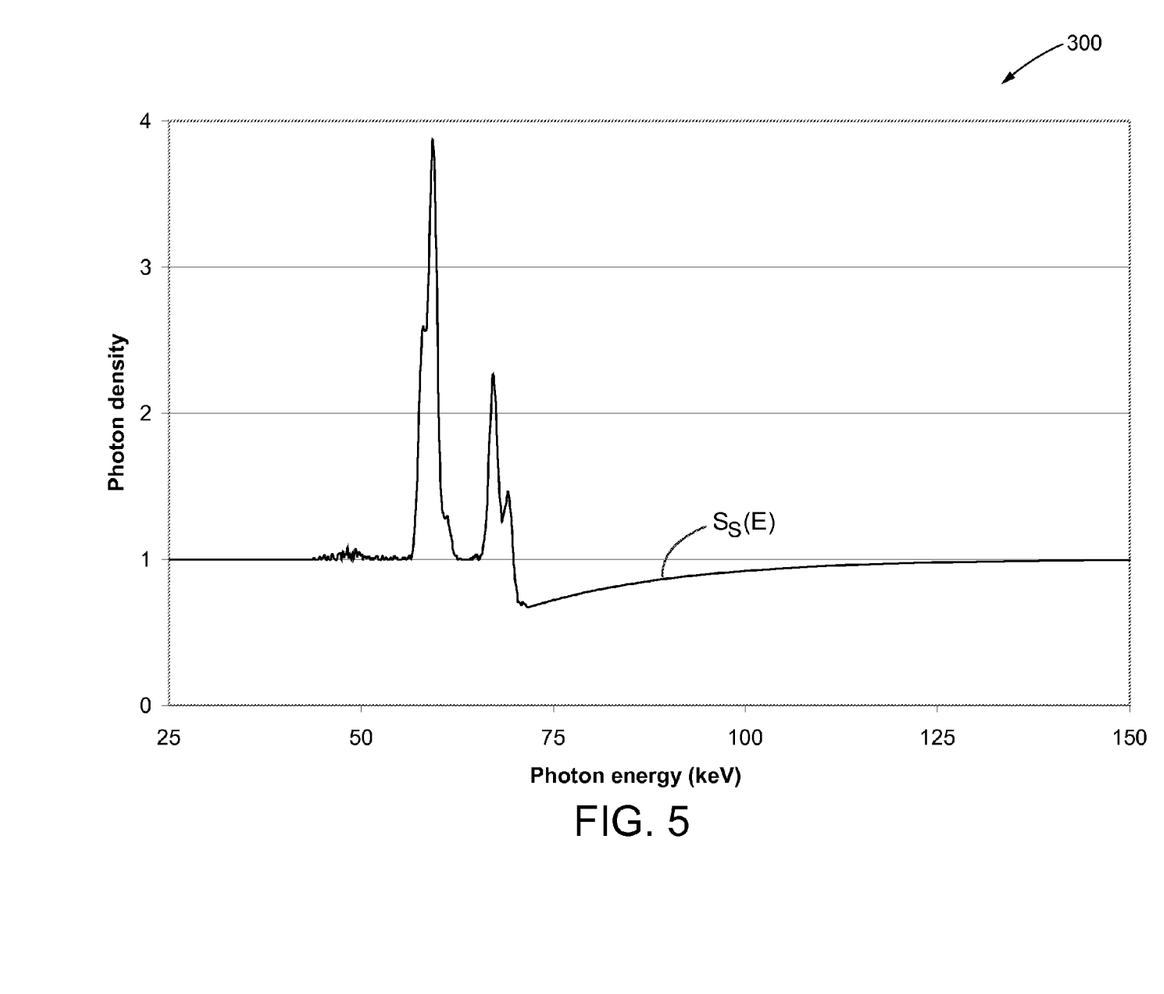
FIG. 5 is a graph of a spectral-correction function that may be used with the method shown in FIG. 3.
Figure 6:
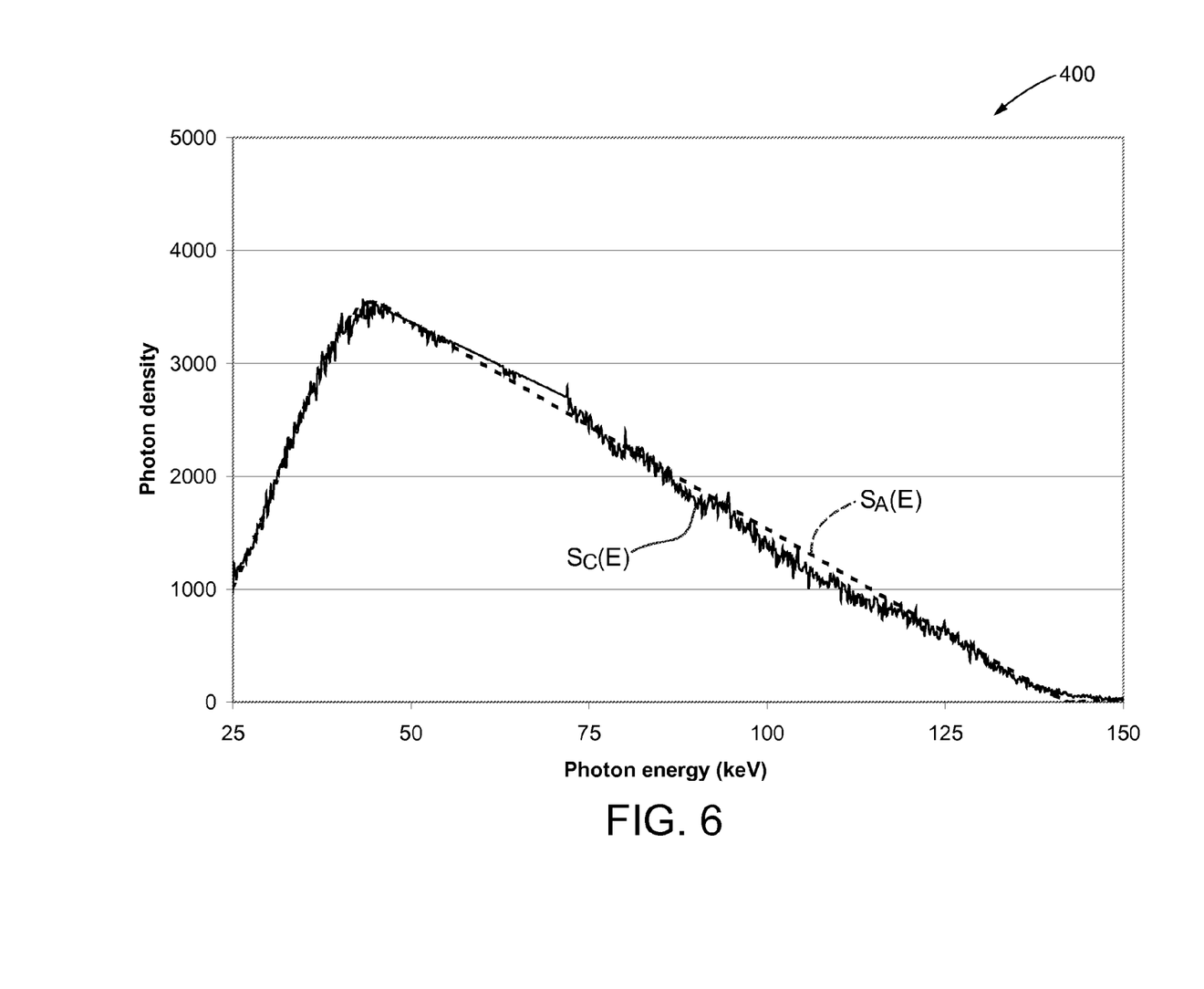
FIG. 6 is a graph of a corrected emission spectrum of the tungsten anode tube.

FIG. 4 is a graph 200 of a photon density emission spectrum S(E) of a tungsten anode tube that may be used with detection system 10 (shown in FIGS. 1 and 2). FIG. 5 is a graph 300 of a spectral-correction function $S_s(E)$ that may be used with method 100 (shown in FIG. 3). FIG. 6 is a graph 400 of a corrected emission spectrum $S_C(E)$ of the tungsten anode tube. Spectral-correction procedure 102 of method 100 can also be referred to as an energy-based correction procedure and/or a noise-correction procedure. Although spectral-correction procedure 102 is described herein with respect to detection system 10, spectral-correction procedure 102 can be used with any suitable system that produces an XRD profile of a scanned object.

Referring to FIGS. 3 and 4, in the exemplary embodiment, spectral-correction procedure 102 includes obtaining 106 an emission spectrum S(E) of anode 15 (shown in FIGS. 1 and 2). Emission spectrum S(E) is also referred to herein as a primary spectrum. Emission spectrum S(E) includes a Kα peak 202, a Kβ peak 204, and a K edge 206. Kα peak 202, Kβ peak 204, and/or K edge 206 of emission spectrum S(E) may cause non-uniformity in measured spectra generated using anode 15. As such, spectral-correction procedure 102 is configured to remove Kα peak 202, Kβ peak 204, and K edge 206 from emission spectrum S(E) so Kα peak 202, Kβ peak 204, and K edge 206 will not adversely affect measured spectra.

Spectral-correction procedure 102 derives corrected emission spectrum $S_C(E)$ that is free of K structures from an original emission spectrum S(E) by dividing emission spectrum S(E) into three energy bands. More specifically, windows 208, 210, and 202 are defined 108 on emission spectrum S(E) based on energies of the spectral structures of emission spectrum S(E). In the exemplary embodiment, a first window 208 is defined 108 from a beginning point 214 of emission spectrum S(E) to a center 216 of Kβ peak 204 ($E_0 \leq E \leq E_1$), a second window 210 is defined 108 from center 216 of Kβ peak 204 to an end 208 of K edge 206 ($E_1 \leq E \leq E_2$), and a third window 212 is defined 108 from end 218 of K edge 206 to an end point 220 of emission spectrum S(E) ($E_2 \leq E \leq E_E$). In the exemplary embodiment, energy $E_1$ is approximately equal to 67.5 kilo-electron volts (keV) and energy $E_2$ is approximately equal to 71.8 keV. Once windows 208, 210, and 212 are defined 108, windows 208, 210, and 212 are used to calculate 110 spectral-correction function $S_s(E)$ (shown in FIG. 5). More specifically, a piecewise spectral-correction function $S_s(E)$ is calculated 110 using spectral structures, such as Kα peak 202, Kβ peak 204, and K edge 206, in emission spectrum S(E). Spectral-correction function $S_s(E)$ includes an equation portion corresponding to each defined window 208, 210, and 212.

Within first window 208, spectral bands 222 and 224 are defined on either side of Kα peak 202. For example, first spectral band 222 is defined between energy $E_3$ and energy $E_4$, and second spectral band 224 is defined between energy $E_5$ and energy $E_6$. Knowledge of the anode material, such as tungsten, and the energy of its characteristic lines permits spectral bands 222 and 224 to be located accurately. As an example for tungsten emission spectrum S(E), low-energy spectral band 222 is defined between energy $E_3$ that is approximately equal to 54 keV and energy $E_4$ that is approximately equal to 56 keV, and high-energy spectral band 224 is defined between energy $E_5$ that is approximately equal to 63.5 keV and energy $E_6$ that is approximately equal to 65.5 keV. An average number of photon counts in each spectral band 222 and 224 is determined and a straight line L(E) is fit through centers of spectral bands 222 and 224. Control system 46 (shown in FIGS. 1 and 2) stores straight line parameters, such as a gradient M and an intercept C with an intensity axis.

To calculate 110 spectral-correction function $S_s(E)$ within first window 208, emission spectrum S(E) from energy $E_0$ to energy $E_1$ is divided by a corresponding value of straight line L(E) at each energy value. If the result of the division is less than unity (e.g. 1), for example 0.5, spectral-correction function $S_s(E)$ is set to unity. As such, in regions of Kα peak 202 and Kβ peak 204, a value of spectral-correction function $S_s(E)$ is greater than unity. Spectral-correction function $S_s(E)$ from energy $E_0$ to energy $E_1$ is generally equal to unity and only the K lines are superimposed. In mathematical form, spectral-correction function $S_s(E)$ within first window 208 is calculated 110 as:

$$S_s(E) = \begin{cases} 1, & \text{if } S(E) \leq L(E) \\ \dfrac{S(E)}{L(E)}, & \text{if } S(E) > L(E) \end{cases}. \quad \text{(Eq. 4)}$$

As such, a first window portion of spectral-correction function $S_s(E)$ is defined using the ratio of emission spectrum S(E) to straight line L(E) and unity according to Equation 4.

Within second window 210, the ratio of amplitude of emission spectrum S(E) to that of straight line L(E), whether greater or less than unity, is evaluated and stored by control system 46 as spectral-correction function $S_s(E)$. In mathematical form, spectral-correction function $S_s(E)$ within second window 210 is calculated 110 as:

$$S_s(E) = \frac{S(E)}{L(E)}. \quad \text{(Eq. 5)}$$

As such, a second window portion of spectral-correction function $S_s(E)$ is defined as the ratio of emission spectrum S(E) to straight line L(E).

Within third window 212, an average number of photon counts is determined by control system 46. A ratio of the average number of photon counts to a height of straight line L(E) is stored as a K-edge ratio $K_R$ by control system 46. In a particular embodiment, K-edge ratio $K_R$ is equal approximately 0.67. To calculate 110 spectral-correction function $S_s(E)$, a numerical difference between unity and K-edge ratio $K_R$ is multiplied by a function that is unity at energy $E_2$ and exponentially decreases with increasing photon energy. In mathematical form, spectral-correction function $S_s(E)$ within third window 212 is calculated 110 as:

$$S_s(E) = 1 - (1 - K_R) \cdot \{\exp\bigl(-(E - E_2) \cdot \gamma\bigr)\} \quad \text{(Eq. 6)}$$

where γ is a factor that describes a speed of relaxation based on a material of anode 15. More specifically, at K edge 206, spectral-correction function $S_s(E)$ has a value equal to K-edge ratio $K_R$ and increasingly approaches unity as the energy above K edge 206 increases. The approach of spectral-correction function $S_s(E)$ to unity is considered to the relaxation associated with factor γ in Equation 6. In a particular embodiment, factor γ is equal to approximately 0.1. In the exemplary embodiment, a third window portion of spectral-correction function $S_s(E)$ is defined as the multiplication in Equation 6.

Calculation 110 yields a piecewise spectral-correction function $S_s(E)$ in the form shown in FIG. 5 when spectral-correction procedure 102 is implemented on emission spectrum S(E) from a tungsten anode bombarded by electrons of 150 keV. An increase in photon noise from Equation 1 when spectral-correction function $S_s(E)$ is used is about 12%. Such an increase in noise is approximately 20 times smaller than an increase in noise using the conventional procedure. Referring to FIG. 6, a corrected emission spectrum $S_C(E)$ is generated by dividing original emission spectrum S(E) by spectral-correction function $S_s(E)$. An approximation of a corrected emission spectrum $S_A(E)$ is shown as a dashed line. In the exemplary embodiment, approximation $S_A(E)$ is calculated using the Kuhlenkampff equation. As can be seen from FIG. 6, by applying spectral-correction function $S_s(E)$ to original emission spectrum S(E), Kα peak 202, Kβ peak 204, and K edge 206 are removed from corrected emission spectrum S$_C$(E).

Referring again to FIGS. 1-3, object 12 is scanned by detection system 10 to obtain 112 a measured spectrum of object 12. Spectral-correction function S$_s$(E) is applied 114 to the measured spectrum to remove effects of Kα peak 202, Kβ peak 204, and K edge 206 (all shown in FIG. 4) from the measured spectrum. More specifically the measured spectrum is divided by spectral-correction function S$_s$(E) to generate a spectrally-corrected measured spectrum. The spectrally-corrected measured spectrum can then be compared 116 to reference XRD profiles or can be further corrected using angular-correction procedure 104.

Figure 7:
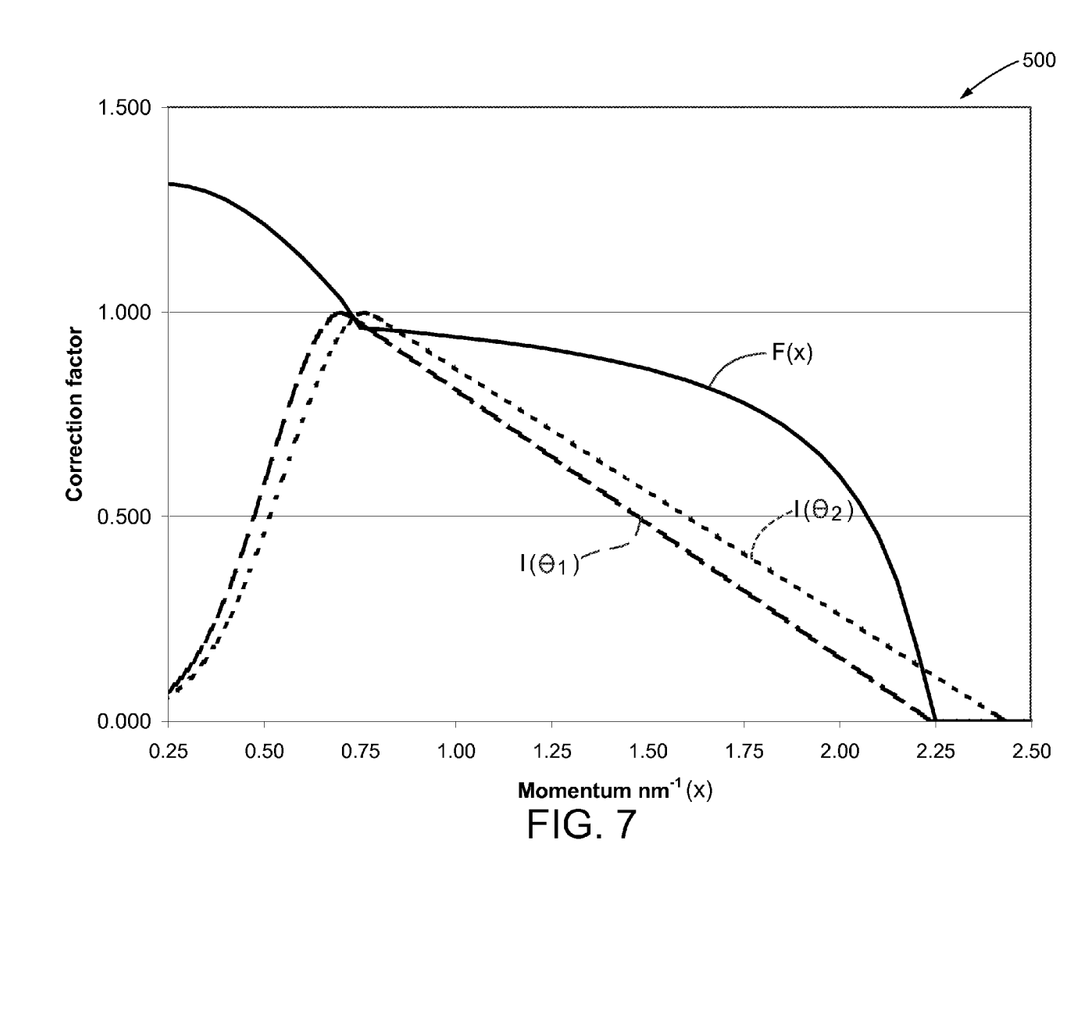
FIG. 7 is a graph of approximated emission spectra and an angular-correction function.

FIG. 7 is a graph of approximated emission spectra I(θ$_1$) and I(θ$_2$) and an angular-correction function F(x). Angular-correction procedure 104 of method 100 can also be referred to as a scatter-angle-based correction method. Although angular-correction procedure 104 is described herein with respect to detection system 10 (shown in FIGS. 1 and 2), angular-correction procedure 104 can be used with any suitable system that produces an XRD profile of a scanned object. Angular-correction procedure 104 first converts an abscissa scale of an XRD spectrum into a momentum scale at a known scatter angle of the XRD spectrum. An intensity of the XRD spectrum is then multiplied by angular-correction function F(x) that transforms an ordinate scale of the XRD spectrum into a scale measured at a smaller and/or different scatter angle. As such, angular-correction procedure 104 allows a common library of XRD profiles, for example known profiles of threat substances, at a particular scatter angle, such as reference scatter angle θ$_R$, to be used for all measured spectra, irrespective of scatter angle. Further, angular-correction procedure 104 allows XRD profiles pertaining to a certain object voxel, measured with varying scatter angle, to be combined by simple addition.

More specifically, in photon emission spectrum S(E) (shown in FIG. 4) of a tungsten anode electron impact X-ray source, Kα peak 202, Kβ peak 204, and K edge 206 (all shown in FIG. 4) are clearly visible in emission spectrum S(E). When primary emission spectrum S(E) is corrected using spectral-correction procedure 102, the K structures are removed and a measured XRD spectrum is equivalent to an XRD spectrum that would have been obtained had primary emission spectrum S(E) had the form of corrected emission spectrum S$_C$(E) (shown in FIG. 6). Angular-correction procedure 104 can then be performed on a spectrally-corrected measured spectrum.

Referring to FIGS. 3 and 7, angular-correction procedure 104 includes obtaining 118 a first calibration spectrum I(θ$_1$) at a first scatter angle θ$_1$. More specifically, a calibration substance is scanned and scattered radiation at first scatter angle θ$_1$ is detected to generate first calibration spectrum I(θ$_1$). Similarly, a second calibration spectrum I(θ$_2$) is obtained 120 at a second scatter angle θ$_2$ by scanning the same calibration substance and detecting scattered radiation at second scatter angle θ$_2$.

Using first calibration spectrum I(θ$_1$) and second calibration spectrum I(θ$_2$), an angular-correction function F(x) is calculated 122. More specifically, angular-correction function F(x) is calculated 122 by dividing first calibration spectrum I(θ$_1$) by second calibration spectrum I(θ$_2$). In mathematical form, angular-correction function F(x) is calculated 122 as:

$$F(x) = \frac{I(\theta_1)}{I(\theta_2)}. \quad \text{(Eq. 6)}$$

Referring to FIG. 3, assuming that the measured spectrum was obtained 112 at second scatter angle θ$_2$ and the reference XRD profiles were obtained at first scatter angle θ$_1$, angular-correction function F(x) is applied 124 to the spectrally-corrected measured spectrum to generate a final corrected measured spectrum. More specifically, by applying 124 angular-correction function F(x) to the spectrally-corrected measured spectrum, the spectrally-corrected measured spectrum is transformed from second scatter angle θ$_2$ to first scatter angle θ$_1$ for comparison 116 with the reference XRD profiles. As such, a substance of object 12 (shown in FIG. 2) can be identified based on the comparison 116. Detection system 10 can then alarm and/or otherwise notify personnel of the identified substance.

The embodiments described herein provide correction procedures for spectral structures and variations of scatter angle in XRD spectra. More specifically, the spectral-correction procedure described herein effectively removes spectral structures from a primary emission spectrum while minimizing any noise introduced into a measured spectrum. Further, the above-described angular-variation correction procedure transforms all XRD profiles to have identical momentum scales and intensity distributions, irrespective of the actual angle of scatter, requires only one set of XRD library profiles for all scatter angles, which speeds processing and reduces storage requirements, and allows all XRD profiles belonging to the same object voxel to be combined with one another by a simple addition operation.

A technical effect of the systems and methods described herein includes at least one of: (a) obtaining an emission spectrum of the anode using the control system, the emission spectrum including spectral structures; (b) calculating a piecewise spectral-correction function using the spectral structures in the emission spectrum; (c) obtaining a measured spectrum of an object; (d) applying the spectral-correction function to the measured spectrum to generate a spectrally-corrected measured spectrum; and (e) correcting the spectrally-corrected measured spectrum for variation in scatter angle.

Exemplary embodiments of systems and methods for correcting X-ray diffraction profiles are described above in detail. The methods and systems are not limited to the specific embodiments described herein, but rather, components of systems and/or steps of the methods may be utilized independently and separately from other components and/or steps described herein. For example, the methods may also be used in combination with other imaging systems and methods, and are not limited to practice with only the detection systems and methods as described herein. Rather, the exemplary embodiment can be implemented and utilized in connection with many other data correction applications.

By way of example and not limitation, computer readable media include computer storage media and communication media. Computer storage media store information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

Although described in connection with an exemplary detection system environment, the embodiments described herein are operational with numerous other general purpose or special purpose computing system environments or configurations. Examples of well known computing systems, environments, and/or configurations that may be suitable for use with aspects of the disclosure include, but are not limited to, mobile computing devices, personal computers, server computers, hand-held or laptop devices, multiprocessor systems, microprocessor-based systems, programmable electronics, mobile telephones, network PCs, minicomputers, mainframe computers, distributed computing environments that include any of the above systems or devices, and the like.

Embodiments of the disclosure may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the embodiments may be implemented with any number and organization of such components or modules. For example, aspects of the embodiments are not limited to the specific computer-executable instructions or the specific components or modules illustrated in the figures and described herein. Other embodiments of the disclosure may include different computer-executable instructions or components having more or less functionality than illustrated and described herein.

Aspects of the disclosure transform a general-purpose computer into a special-purpose computing device when configured to execute the instructions described herein. Further, the order of execution or performance of the operations in embodiments illustrated and described herein is not essential, unless otherwise specified. That is, the operations may be performed in any order and/or simultaneously, unless otherwise specified, and embodiments may include additional or fewer operations than those disclosed herein. For example, it is contemplated that executing or performing a particular operation before, contemporaneously with, or after another operation is within the scope of aspects of the disclosure.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for correcting an X-ray diffraction (XRD) profile measured by an X-ray diffraction imaging (XDi) system that includes an anode, a detector, and a control system, said method comprising:
    obtaining an emission spectrum of the anode using the control system, the emission spectrum including spectral structures including a K$\alpha$ peak, a K$\beta$ peak, and a K edge;
    calculating a piecewise spectral-correction function using the spectral structures in the emission spectrum comprising defining a plurality of windows of the emission spectrum based on energies of the spectral structures at least partially as a function of the K$\beta$ peak and the K edge;
    obtaining a measured spectrum of an object; and
    applying the spectral-correction function to the measured spectrum to generate a spectrally-corrected measured spectrum.

2. A method in accordance with claim 1, wherein defining the plurality of windows of the emission spectrum at least partially as a function of the K$\beta$ peak and the K edge comprises:
    defining a first window from a beginning point of the emission spectrum to a center of the K$\beta$ peak;
    defining a second window from the center of the K$\beta$ peak to an end of the K edge; and
    defining a third window from the end of the K edge to an end point of the emission spectrum.

3. A method in accordance with claim 2, wherein calculating a piecewise spectral-correction function further comprises:
    defining a spectral band on each side of the K$\alpha$ peak;
    fitting a straight line to the spectral bands;
    calculating a ratio of the emission spectrum to the straight line; and
    defining a first window portion of the piecewise spectral-correction function using the ratio and unity.

4. A method in accordance with claim 3, wherein calculating a piecewise spectral-correction function comprises defining a second window portion of the piecewise spectral-correction function as the ratio of the emission spectrum to the straight line.

5. A method in accordance with claim 3, wherein calculating a piecewise spectral-correction function comprises:
    calculating a K edge ratio of an average number of photon counts to a height of the straight line;
    multiplying a numerical difference between unity and the K edge ratio by a function that is unity at an energy of the K edge and exponentially decreases with increasing photon energy; and
    defining a third window portion of the piecewise spectral-correction function as the multiplication.

6. A method in accordance with claim 1, wherein applying the spectral-correction function to the measured spectrum further comprises dividing the measured spectrum by the spectral-correction function to generate the spectrally-corrected measured spectrum.

7. A method in accordance with claim 1 further comprising correcting the spectrally-corrected measured spectrum for variation in scatter angle.

8. A method in accordance with claim 7, wherein correcting the spectrally-corrected measured spectrum for variation in scatter angle comprises:
    obtaining a first calibration spectrum that is generated by scanning a calibration substance and detecting scattered radiation at a first scatter angle;

obtaining a second calibration spectrum that is generated by scanning the calibration substance and detecting scattered radiation at a second scatter angle different than the first scatter angle; and calculating an angular-correction function using the first calibration spectrum and the second calibration spectrum.

9. A method in accordance with claim 8, wherein calculating an angular-correction function comprises dividing the first calibration spectrum by the second calibration spectrum.

10. A method in accordance with claim 8, wherein the spectrally-corrected measured spectrum is detected at the second scatter angle, said method further comprising applying the angular-correction function to the spectrally-corrected measured spectrum to transform spectrally-corrected measured spectrum from the second scatter angle to the first scatter angle.

11. A control system for use with an X-ray diffraction imaging (XDi) system comprising a radiation source configured to generate a primary beam of radiation, the radiation source comprising an anode, and a detector configured to detect radiation scattered by an interaction of the primary beam with an object, said control system configured to:
obtain an emission spectrum of the anode, the emission spectrum including spectral structures including a Kα peak, a Kβ peak, and a K edge;
calculate a piecewise spectral-correction function using the spectral structures in the emission spectrum comprising defining a plurality of windows of the emission spectrum based on energies of the spectral structures at least partially as a function of the Kβ peak and the K edge;
obtain a measured spectrum of an object; and
apply the spectral-correction function to the measured spectrum to generate a spectrally-corrected measured spectrum.

12. A control system in accordance with claim 11 further configured to correcting the spectrally-corrected measured spectrum for variation in scatter angle.

13. A control system in accordance with claim 11, wherein and a K edge, said control system configured to define a plurality of windows of the emission spectrum based on energies of the spectral structures at least partially as a function of the Kβ peak and the K edge further configured to define a first portion, a second portion, and a third portion of the piecewise spectral-correction function based on energies of the Kα peak, the Kβ peak, and the K edge.

14. A control system in accordance with claim 13 further configured to:
define a spectral band on each side of the Kα peak;
fit a straight line to the spectral bands;
calculate a ratio of the emission spectrum to the straight line; and
define the first portion of the piecewise spectral-correction function using the ratio and unity.

15. A control system in accordance with claim 13 further configured to define the second portion of the piecewise spectral-correction function as a ratio of the emission spectrum to a straight line, the straight line fit to spectral bands adjacent to the Kα peak.

16. A control system in accordance with claim 13 further configured to:
calculating a K edge ratio of an average number of photon counts to a height of a straight line that is fit to spectral bands adjacent to the Kα peak;
multiplying a numerical difference between unity and the K edge ratio by a function that is unity at an energy of the K edge and exponentially decreases with increasing photon energy; and
defining the third portion of the piecewise spectral-correction function as the multiplication.

17. An X-ray diffraction imaging (XDi) system comprising:
a radiation source configured to generate a primary beam of radiation, said radiation source comprising an anode;
a detector configured to detect radiation scattered by an interaction of the primary beam with an object; and
a control system coupled in communication with said detector, said control system configured to:
obtain a measured spectrum detected by said detector at a first scatter angle;
perform a spectral-correction procedure on the measured spectrum to remove spectral structures from an emission spectrum of said anode; and
perform an angular-correction procedure on the measured spectrum to transform the measured spectrum from the first scatter angle to a second scatter angle comprising:
obtaining a first calibration spectrum that is generated by scanning a calibration substance and detecting scattered radiation at a first scatter angle;
obtaining a second calibration spectrum that is generated by scanning the calibration substance and detecting scattered radiation at a second scatter angle different than the first scatter angle;
calculating an angular-correction function by dividing the first calibration spectrum by the second calibration spectrum; and
applying the angular-correction function to the measured spectrum.

18. An XDi system in accordance with claim 17, wherein said control system is configured to perform the spectral-correction procedure by:
calculating a piecewise spectral-correction function using energies of the spectral structures in the emission spectrum; and
applying the spectral-correction function to the measured spectrum.

* * * * *